United States Patent
Dall et al.

(10) Patent No.: US 6,928,900 B2
(45) Date of Patent: Aug. 16, 2005

(54) TOOL FOR SHEARING BOLTS

(75) Inventors: Vagn-Erik Dall, Maidenhead (GB); David J. Reed, Sheffield (GB); Peter Lawes, Maidenhead (GB)

(73) Assignee: V O Design and Innovation Limited (GB)

(*) Notice: Subject to any disclaimer, the term of this patent is extended or adjusted under 35 U.S.C. 154(b) by 0 days.

(21) Appl. No.: 10/760,932

(22) Filed: Jan. 20, 2004

(65) Prior Publication Data

US 2004/0144211 A1 Jul. 29, 2004

Related U.S. Application Data

(63) Continuation of application No. 09/762,029, filed as application No. PCT/GB99/02558 on Aug. 4, 1999, now abandoned.

(30) Foreign Application Priority Data

Aug. 4, 1998 (GB) .............................................. 9816962

(51) Int. Cl.⁷ .............................................. B25B 13/00
(52) U.S. Cl. .......................................... 81/52; 81/488
(58) Field of Search ........................ 81/52, 124.4, 125, 81/488

(56) References Cited

U.S. PATENT DOCUMENTS

| | | | |
|---|---|---|---|
| 3,255,940 A | 6/1966 | Ridenour | |
| 3,698,231 A | * 10/1972 | Davis, Jr. | 29/566.1 |
| 4,299,519 A | * 11/1981 | Corbett | 29/243.522 |
| 4,589,155 A | 5/1986 | Jeal | |
| 4,699,552 A | 10/1987 | Jeal | |
| 5,470,118 A | 11/1995 | Burton | |
| 5,653,710 A | 8/1997 | Haerle | |
| 5,720,751 A | 2/1998 | Jackson | |
| 5,725,541 A | 3/1998 | Anspach, III et al. | |
| 5,741,282 A | 4/1998 | Anspach, III et al. | |
| 5,819,846 A | 10/1998 | Bolt, Jr. | |
| 6,257,331 B1 | 7/2001 | Blount et al. | |

FOREIGN PATENT DOCUMENTS

DE    2261281    6/1974

* cited by examiner

Primary Examiner—Joseph J. Hail, III
Assistant Examiner—David B. Thomas
(74) Attorney, Agent, or Firm—Wallenstein Wagner & Rockey, Ltd.

(57) ABSTRACT

A tool for breaking a shaft includes two aligned tubular elements (20, 22), each having an end portion for receiving a contiguous length of the same shaft (2). Means are provided for locking each end portion against rotation relative to the shaft length received therein, and the elements are adapted for rotation relative to one another with the end portions so locked, to relatively twist the shaft lengths and shear the lengths at the interface between them. The element end portions will normally have juxtaposed faces, and it is preferred that the faces are moved towards each other during the relative rotation and as the shaft lengths are twisted relative to each other. This assists in achieving a substantially planar face at the fracture plane. A compressible washer may be disposed between the juxtaposed faces. This can stabilize the moving parts as the shaft is broken, although normally screw threads on the tubular elements will effect the movement of the element. towards each other, and this in itself may provide sufficient stability.

12 Claims, 2 Drawing Sheets

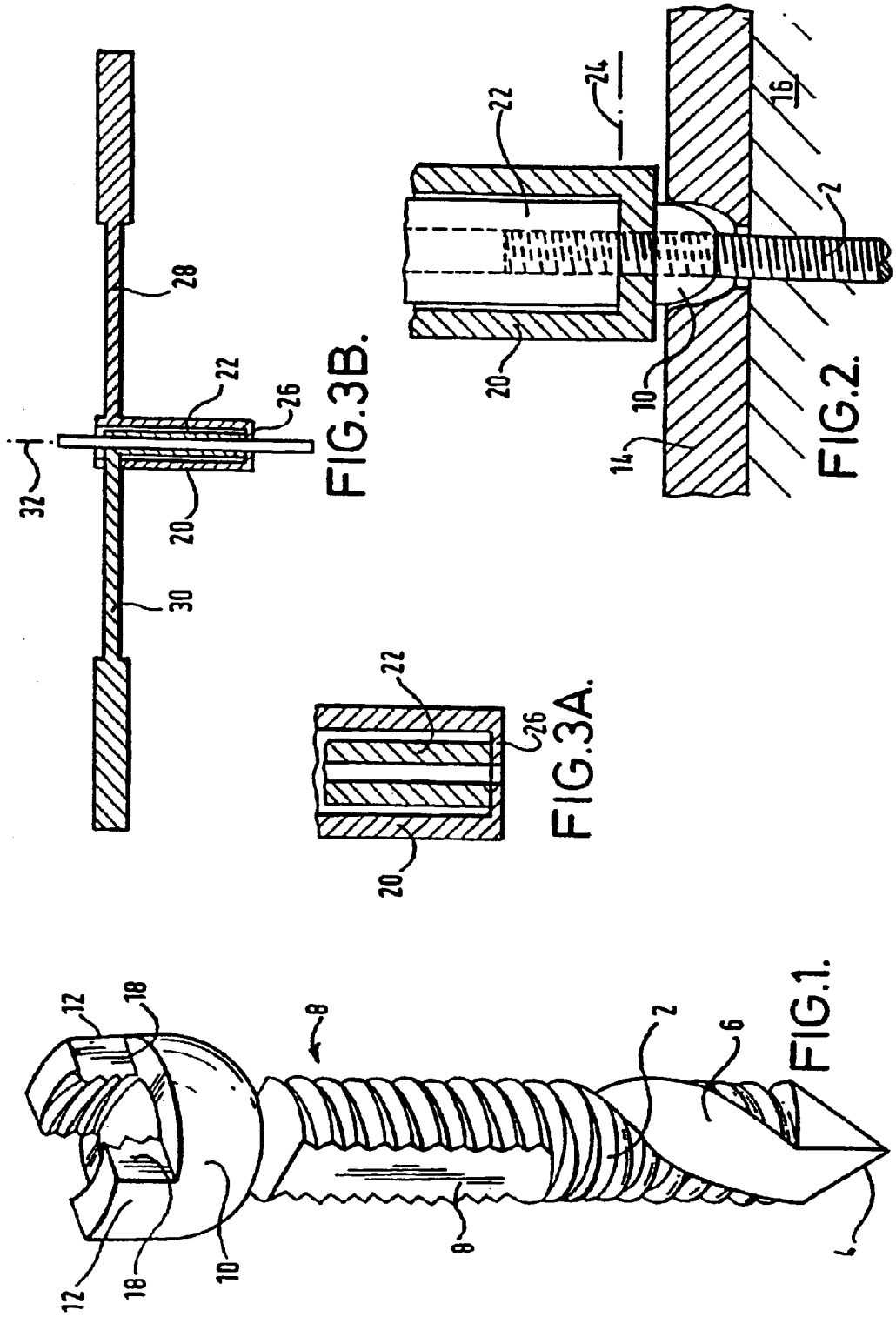

TOOL FOR SHEARING BOLTS

RELATED APPLICATION

This is a continuation application of U.S. patent application Ser. No. 09/762,029, now abandoned which is a §371 of International Patent Application No. PCT/GB99/02558, filed 4 Aug. 1999, claims priority from British Application No. GB9816962.6, filed 4 Aug. 1998 entitled "Tool for Shearing Bolts". These applications are incorporated herein by reference.

TECHNICAL FIELD

This invention relates to the breaking of shafts, nomally metallic shafts, in which contiguous shaft lengths are twisted relative to one another to break the shaft along a fracture plain. The invention has particular application to lockable screw assemblies in which a shaft is broken at a fracture plane substantially aligned to the exposed surface of a nut located and typically locked thereon. This Application is of especial value in surgical applications where such a screw assembly is used as a cortical bone screw whose length is immediately adaptable to an individual situation.

BACKGROUND OF THE INVENTION

In a number of fields there is a need for screws and bolts which can be used to a given, undefined length, but which cannot tolerate a length of screw projecting from an exposed surface. Particularly in surgical situations it has been necessary to carefully select a cortical bone screw of the right length in order to ensure that a plate may be attached to a bone with a substantially smooth surface at the exposed face of the plate.

SUMMARY OF THE INVENTION

According to the present invention, a tool for breaking a shaft comprises two aligned tubular elements, each having an end portion for receiving a contiguous length of the same shaft. Means are provided for locking each end portion against rotation relative to the shaft length received therein, and the elements are adapted for rotation relative to one another with the end portions so locked, to relatively twist the shaft lengths and shear the lengths at the interface between them. The element end portions will normally have juxtaposed faces, and it is preferred that the faces are moved towards each other during the relative rotation and as the shaft lengths are twisted relative to each other. This assists in achieving a substantially planar face at the fracture plane. A compressible washer may be disposed between the juxtaposed faces. This can stabilize the moving parts as the shaft is broken, although normally screw threads on the tubular elements will effect the movement of the element towards each other, and this in itself may provide sufficient stability.

The tubular elements in tools according to the invention will normally be co-axially aligned. However, there can be some benefit in having the shaft to be broken installed in the tool along an axis offset from the common axis of the operative elements. This generates some additional shear forces in the shaft contributing to the creation of a flat surface along the fracture plane, although it will be appreciated that the increase of shear forces at one point in the cross section of the shaft will of course result in a decrease of the shear forces at opposite location on the fracture plane. In these arrangements, whether or not the shaft is disposed eccentrically relative to the tubular elements, the tubular elements are preferably themselves telescopically engaged, thereby assisting in the preservation of the co-axial alignment.

Different techniques may be used to lock the contiguous length of the shaft relative to the respective elements of the tool. One mechanism comprises a gripping component at the end of each tubular element, with a sleeve disposed therebetween. The sleeve has convergant frustoconical surfaces aligned with the gripping components, and means are provided for urging the components towards one another over the frustoconical surfaces, and thereby radially inward to engage and grip a shaft. In a preferred embodiment, the gripping components are disposed between the juxtaposed faces of the tubular elements, as such that as the tubular elements move towards each other as they are relatively rotated, the gripping elements are activated into engaging a shaft.

The gripping components in the above-described mechanism can each take the form of an annular array of cranate segments with gripping surfaces directed towards the shaft. This type of mechanism is particularly suited to use on shafts with irregular outer surfaces, such as those bearing a screw thread. As the gripping components engage the shaft, they can cut into this surface or threads to ensure effective contact is made. If the shaft has an overall non-circular cross-section, then the configuration of the gripping components can be correspondingly adapted.

Another locking mechanism relies on the specific provision in the end portions of the tubular elements of openings and matching the cross section of the shaft, which itself has to be non-circular. With the tool in place, and the shaft received in the openings in the end portions of both elements, relative rotation of the tubular elements imposes corresponding relative rotation on the shaft resulting in breakage of the shaft along a fracture plane corresponding to the abutment between the respective end portions. This variant of the invention has particular relevance to the surgical applications referred to above in which a nut is located on the threaded shaft and is to be locked at a selected axial location. In this variant, a tool according to the invention can be adapted to be used for breaking a threaded shaft bearing a nut, the shaft having an external form thereon in at least two axially extending arc sections. The nut has an axial end section complementing the non-circular section of the shaft, forming therewith one orientation, an extended non-circular cross section matching that of the opening in the end portion of one tubular element of the tool. The cross section of the shaft itself, of course, matches the opening in the end portion of the other element. In a particular use of the above machine, the present invention also provides a screw assembly comprising a screw and a nut, and in which the nut can be readily located and locked at a selected axial location, and the shaft simultaneously broken at a face of the nut to leave a substantially smooth surface. The shaft has an external screw thread formed in at least two axially extending, normally parallel arc sections. The nut has a complementary internal screw thread, also in at least two arc sections, and the respective thread sections of the shaft and nut are capable of misalignment such that the nut can move translationally along the shaft without rotation, or at least without rotation with the threads engaged. With the nut close to its intended final position, it may be rotated to bring the threads into engagement, and over an extent of angular rotation to permit final tightening of the nut against the surface. The nut has an extended portion of cross-section which combines with that of the shaft when the nut is at its full extent of angular rotation to have a cross-section which can be engaged by the first element of a tool. The length of shaft projecting from the extended portion of the nut can be engaged by a second element of the tool, and with the junction between the first and second elements of the tool being close to the exposed face of the extended portion of the nut, the two elements can be rotated relative to one another to break the shaft substantially at the end face of the extended nut portion. The screw thread on the shaft will normally have two axially extending diametrically opposed arc sections, with substantially parallel flanks therebetweenl. The extended portion of the nut in such an arrangement will comprise two castellations for alignment with the threaded arc sections at its full extend of angular orientation on the shaft.

We have found that in the practice of the invention, during relative rotation of the elements to twist a projecting length of shaft relative to the adjacent length thereof, shear forces are generated substantially at the plane of the twist with the result that the shaft in this plane is progressively work hardened or embrittled, and eventually broken at this plane. The same phenomenon is apparent whether or not a nut is present on the shaft. The extent and number of relative rotational movements of the two elements that is required to achieve a fracture will of course depend upon the material of the shaft and its dimensions, and upon the rate of relative rotation. Generally, the slower the rate of rotation the better the work hardening effect and the smoother the surface formed at the fracture plane.

In addition to providing a means by which a threaded shaft can be cleanly broken at the end face of the nut, the invention also provides a means by which the threads of the shaft and nut are effectively locked to prevent relative rotation. As the projecting shaft length is twisted relative to the shaft confined in the nut, the threads on the shaft plastically deform into irregular engagement with the threads on the nut effectively locking the nut against rotation relative to the shaft. This provides additional security for an installed assembly, and enables the screw assembly to be locked and broken at the desired fracture plane in effectively a single process.

Pursuant to the above, a method according to the invention of fitting and locking a nut on a threaded shaft in an assembly of the kind just described, typically comprises the following steps:

a) with the threads of the nut and shaft misaligned, translating the nut along the shaft until the nut engages the surface in which the shaft is received;
b) rotating the nut to its full extent of angular rotation;
c) holding the nut and shaft within the nut in their established orientation; and
d) rotating the length of shaft projecting from the extended portion of the nut to twist the shaft within the nut and lock the threads relative to one another, and to break the shaft at the end face of the extended portion of the nut.

A tool for use in the above method comprises two coaxial tubular elements relatively rotatable about their common axes, the outer element having an end with a first cross-section and the inner element having an end with a second cross-section axially spaced from the outer element end. The first cross-section is adapted to fit the combined cross-section of the shaft and extended portion of the nut in the assembly, and the second cross-section is adapted to fit around the shaft Means are provided for rotating the inner and outer elements relative to one another, with their respective ends fitted to the shaft and nut, and to the shaft, to twist the shaft projecting from the nut relative to the shaft within the nut and thereby break the shaft in the plane at the face of the extended portion of the nut. Typically, the rotating means in tools of this invention comprises two arms extending laterally from the common axis of the elements, and in substantially the same plane. In this form, they can be easily held by two hands and brought together to effect an initial twist which serves to work harden or embrittle the material of the shaft at the fracture plane. The arms can then be forced back to their original position in a reverse motion which continues the work hardening or embrittlement process, and these movements can be repeated until the shaft fractures. Slower relative rotation of the tubular elements has been found to result in the formation of a smoother surface at the fracture plane. Generally though, two or three twisting movements over something rather less than 180° is sufficient. Normally, each turning movement will cause relative rotation of the tubular elements over around 135°.

The present invention is generally intended to be embodied in assemblies in which the shaft and nut, if used, are metallic, typically in stainless steel. For medical applications. implant quality steel should be used, a typical standard being 316L comp. D. We have found that shafts with diameters of around 3.5 mm in this material perform well as the basic component of a cortical bone screw embodying the invention, and can fracture cleanly at the exposed plane of the extended portion of the nut in two relative twists of the projecting shaft through 135°. However, the invention can also be useful in breaking shafts found in other materials, including plastics materials, such as ABS.

Other features and advantages of the invention will be apparent from the following specification taken in conjunction with the following drawings.

BRIEF DESCRIPTION OF THE DRAWINGS

The invention will now be described by way of example, and with reference to the accompanying schematic drawings wherein:

FIG. 1 is a perspective view showing an assembly according to the invention comprising the shaft and nut;

FIG. 2 is a longitudinal sectional view through the shaft and nut installed in a plate, and a locking tool disposed thereover;

FIGS. 3A and 3B3 are reduced sectional view illustrating components of the twisting tool;

DETAILED DESCRIPTION OF THE PREFERRED EMBODIMENT

Figure 4:
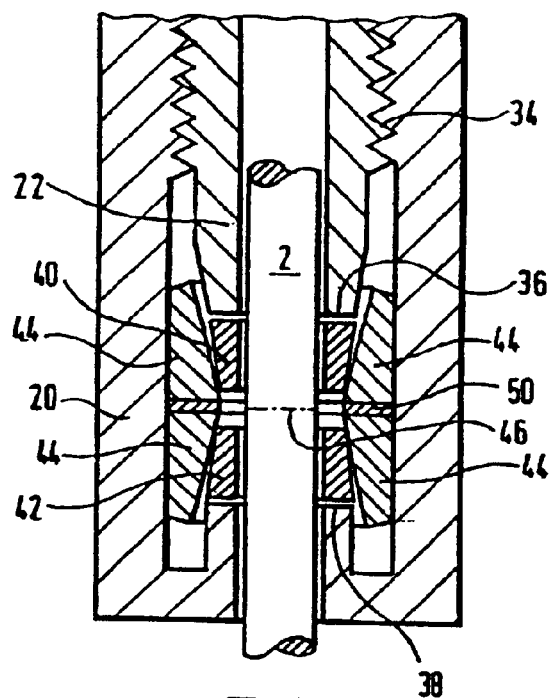
FIG. 4 is an enlarged sectional view illustrating an alternative locking mechanism.

The assembly shown in FIG. 1 consists of a screw 2 having a sharp end 4 from which a removal duct 6 extends to flanks 8 cut parallel into opposite sides of the screw. As can be seen, the flanks are cut well below the root of the screw thread. The nut 10 has a generally hemi-spherical base with two upstanding projections 12 on the inner surfaces whereof are formed internal screw threads corresponding to the external thread on the shaft 2. The peripheral extent of each thread section on the projections 12 of the nut is less than the notional periphery length of the thread cut away to form each flank 8 on the shaft 2. Thus, with the respective threads misaligned, the nut 10 can move translationally along the shaft 2 without any engagement between the threads. However, this is not essential. The assembly does of course function quite effectively with a full thread on the nut, requiring rotation of the nut to effect its translational movement, and this can be preferred in some circumstances.

FIG. 2 shows the shaft 2 installed in the substrate with the nut 10 thereon holding a plate 14 against the substrate. The nut 10 have been moved (translated) along the shaft to the position shown, and a tool (not shown). Is then used to turn the nut 10 on the shaft 2 to bring the respective threads into engagement. This engagement can also serve to finally tighten the nut 10 against the plate 14 to hold it tight against the substrate 16. However, when the threads of the nut are continuously engaged with the threads on the shaft, final tightening may be completed subsequently.

With the nut 10 in its final position, and the respective thread portions on the nut and shaft in full engagement, the flanks 8 on the shaft are aligned with the sides 18 of the nut projections 12. In this orientation the outer tubular element 20 of a locking and breaking tool is fitted over the shaft and nut to hold them in that relative orientation. At the same time, the inner tubular element 22 slides over the projecting length of the shaft 2 engaging the flanks 8. With the inner and outer elements in place, they are turned relative to one another to twist the projecting shaft length relative to the shaft within the nut. This generates shear forces at what would otherwise be the exposed face of the nut projections 12 which serve to initially work harden the metal of the shaft at the plane 24 and eventually break the shaft at that plane. We have found that breaking the shaft in this way results in the substantially smooth surface at the fracture plane, and certainly a surface sufficiently smooth to be tolerated in a surgical situation.

As noted above, the relative twisting of the shaft at the fracture plane 24 not only embrittles and eventually breaks the shaft substantially at the fracture plane, but it also effects plastic deformation of the shaft threads to effectively lock the nut against inadvertent rotation thereafter relative to the shaft. The consequence of this is that when the shaft is broken at the fracture plane, the nut is also locked onto the shaft 2, and the plate 14 thereby safely secured against the substrate 16.

Although the invention has been described above with particular reference to a shaft having planar flanks 8 on opposite sides thereof and the nut having complementary planar surfaces 18 on it projections 12. It will be appreciated that various cross-sections of the shaft and nut can be used. For example, the cross-section of the shaft might be generally cruciform, with the nut and shaft each having four threaded arc sections. The inner cross-sections of the flange 26 on the outer element of the locking and breaking tool and the inner element would of course have to match any modified shaft and nut cross-section.

FIG. 3A shows a detailed view of the coaxial tubular elements of the twisting tool. In the absence of the shaft and nut. As can be seen, the outer element 20 terminates in an inwardly directed flange 26, and it is the inner boundary of this flange 26 that complements the cross-section of the shaft 2 and nut projections 12 when the threads are in full contact. The inner tubular element is wholly within the outer tubular element, at least at this end, and rests or substantially rests on the flange 26 of the outer element 20. The inner element 22 has an internal cross-section corresponding to that of the shaft 2 with planar faces 8.

FIG. 3B shows a further reduced illustration of the entire twisting and breaking tool. As can be seen, each element 20, 22 is coupled to a respective arm or handle 28, 30 which are turned about the common axis 32 of the tubular elements to twist the respective shaft portions relative to one another.

FIG. 4 illustrates an alternative locking mechanism for locking the respective elements 20 and 22 against the contiguous lengths of the shaft 2. Element 22 is received in Element 20, and is coupled thereto by means of a screw thread indicated at 34. Thus, as the tubular elements are turned relative to one and other, their juxtaposed ends 36 and 38 move towards, each other. Between them are two annular gripping components 40 and 42, disposed on convergant frustoconical surfaces of two sleeves 44. Thus, as the end sections 36 and 38 of the elements 20 and 22 move towards each other, the gripping components 40 and 42 are ramped into gripping engagement with contiguous lengths of the shaft 2. As the rotation of the elements 20 and 22 continues, the gripped sections of the shaft are rotated relative to one another resulting ultimately in breakage of the shaft at the fracture plane 46. A washer 50 located between the sleeves 44 substantially at the fracture plane facilitates their relative rotation with the shaft lengths.

Figure 5:
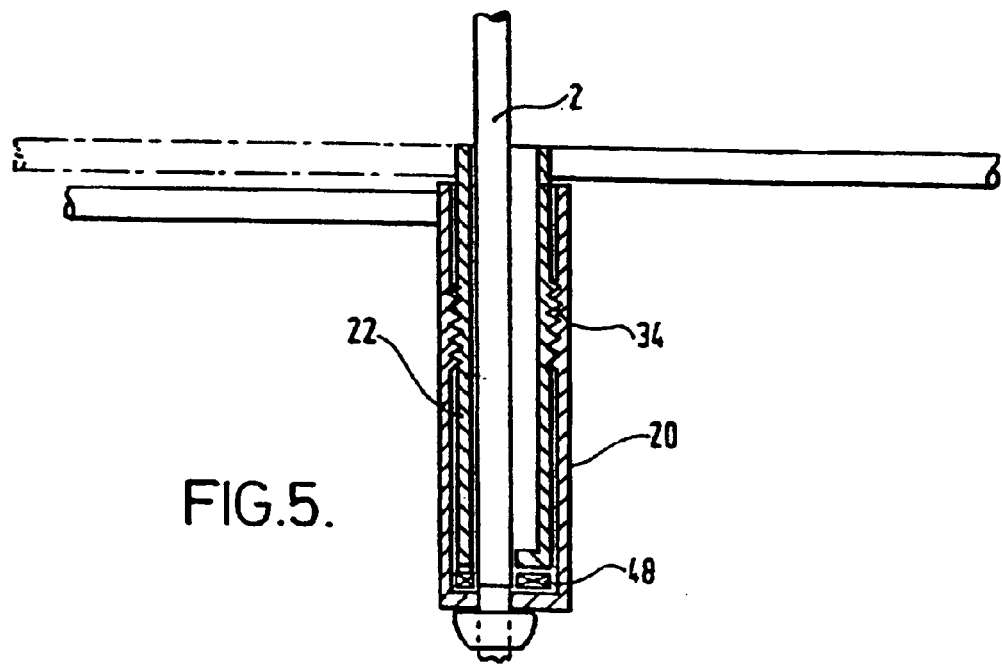
FIG. 5 shows how eccentric movement of the tubular elements in a tool of the invention relative to the shaft, can be generated as the shear system is actuated.

FIG. 5 shows an arrangement in which the openings in the end portions of the tubular elements 20 and 22 are eccentric relative to their common rotational axis, with the result that when a shaft is located in these openings, its rotational axis is spaced from the common axis of the tubular elements. The surfaces of the respective openings jn the end portion of the tubular elements 20 and 22 are formed with gripping surfaces which, as the tubular elements are rotated relative to one another, are forced into engagement with the surface of the shaft 2. The eventual result is that the shaft is broken along a fracture line between the openings in the end portions of the respective tubular elements, as a consequence of this eccentric twisting. In this respect, it will be appreciated that the grip applied to the respective shaft lengths increases as the tubular elements are relatively rotated.

In the embodiment shown in FIG. 5, a compressible washer is disposed around the shaft between the end sections of the respective tubular elements. This provides for the end portions of the tubular elements to move towards each other in a controlled fashion as the elements are rotated relative to each other and break the shaft.

FIG. 5 also illustrates a nut 52 located on the shaft, with an extended section thereof located in the opening in the end portion of the tubular element 20. The extended sections of the nut can have undercuts or dovetailed plugs to provide for some additional axial compression to be applied to threads, partial or complete, formed on the shaft 2.

It will be appreciated that other gripping or locking mechanisms may be used to engage the contiguous shaft lengths, and thereby facilitate its breakage at the fracture plane.

The invention has particular application in surgery, where a bone plate or other element has to be secured against a bone. Screw assemblies according to the invention can be used as cortical bone screws, and the great advantage is of course that a shaft of the same length can be used in each securement. After the hole is initially drilled in the bone, the shaft is fitted to the desired depth using a tool adapted to engage the cross-section of the exposed length, and driven home. The nut is then fitted over the exposed shaft length and translated substantially to its final position, where it is then turned through the requisite angle to finally tighten the nut and create with the nut projections and the shaft the cross-section adapted to be received and fitted in the flange of the outer tubular element of the locking and breaking tool. The tool is then fitted with the inner element engaging only the shaft over the nut, and the tool operated in the manner described above. Initially the threads of the shaft are plastically deformed to lock the nut on the shaft, and as the twisting continues the shaft progressively embrittles at the fracture plane, and eventually breaks to leave a smooth exposed surface.

What is claimed is:

1. A tool for breaking a shaft, comprising two aligned tubular elements having end portions for receiving continuous lengths of said shaft, wherein the tubular elements are engaged one within the other; means for locking each end portion against rotation relative to a shaft length received therein; and means for rotating the elements relative to one another with the end portions so locked to relatively twist the shaft lengths and shear the lengths at the interface between them.

2. A tool according to claim 1 wherein the element end portions have juxtaposed faces.

3. A tool according to claim 2 including means for urging the faces towards each other dining said relative rotation.

4. A tool according to claim 3 wherein the means for urging comprises complementary screw threads on the tubular elements.

5. A tool according to claim 2 including a compressible washer disposed between the juxtaposed faces.

6. A tool according to claim 1 wherein the tubular elements are coaxially aligned.

7. A tool according to claim 6 wherein the element end portions are adapted to receive said shalt along an axis eccentric relative to the common axis of the elements.

8. A tool according to claim 1 wherein locking means comprise a gripping component at the end of each tubular element; a sleeve disposed radially between the tubular elements, the sleeve having convergent frustroconical surfaces aligned with the gripping components; and means for urging the gripping components towards one another over the frustroconcial surfaces and thereby radially inwards to engage and grip said shaft.

9. A tool according to claim 8 wherein the gripping components are disposed between the juxtaposed end faces of the tubular elements.

10. A tool according to claim 1 wherein the end portion of each tubular element has a non-circular opening for receiving said shaft length, for restricting rotation therein of a shaft with a correspondingly non-circular cross section.

11. A tool according to claim 10 for breaking a threaded shaft bearing a nut, the shaft having an external screw thread formed thereon in at least two axially extending arc sections, and the nut having an axial end section complementing the non-circular cross-section of the shaft, forming therewith in one orientation an extended non-circular cross-section matching that of the opening in the end portion of one tubular element, the cross-section of the shaft itself matching the opening in the end portion of the other tubular element.

12. A tool for breaking a shaft assembly according to claim 1, wherein the tool comprises outer and inner coaxial tubular elements and relatively rotatable about their common axis, the outer element having an end with a first cross-section and the inner element having an end with a second cross-section axially spaced from the outer element end, the first cross-section being adapted to fit the combined cross-section of the shaft and extended portion of the nut in said assembly and the second cross-section being adapted to fit around the shaft, means for rotating the inner and outer elements relative to one another with their ends fitted respectively to the shaft and nut, and to the shaft, to twist the shaft projecting from the nut relative to the shaft within the nut to break the shaft in the plane at the face of the extended portion of the nut.

* * * * *